US012708359B2

(12) United States Patent
Petry et al.
(10) Patent No.: US 12,708,359 B2
(45) Date of Patent: Aug. 18, 2026

(54) SUTURE ANCHORS WITH ONE-WAY LOCKING MECHANISMS

(71) Applicant: ARTHREX, INC., Naples, FL (US)

(72) Inventors: Andrew Christian Petry, Naples, FL (US); Peter J. Dreyfuss, Naples, FL (US); Paul C. Brady, Knoxville, TN (US); Philipp Moroder, Meilen (CH)

(73) Assignee: ARTHREX, INC., Naples, FL (US)

( * ) Notice: Subject to any disclaimer, the term of this patent is extended or adjusted under 35 U.S.C. 154(b) by 169 days.

(21) Appl. No.: 18/421,014

(22) Filed: Jan. 24, 2024

(65) Prior Publication Data

US 2025/0228548 A1 Jul. 17, 2025

Related U.S. Application Data

(60) Provisional application No. 63/620,280, filed on Jan. 12, 2024.

(51) Int. Cl.
*A61B 17/04* (2006.01)
*A61F 2/08* (2006.01)
(Continued)

(52) U.S. Cl.
CPC ...... *A61B 17/0401* (2013.01); *A61B 17/0487* (2013.01); *A61F 2/0811* (2013.01); *A61B 2017/00982* (2013.01); *A61B 2017/0404* (2013.01); *A61B 2017/0417* (2013.01); *A61B 2017/0427* (2013.01); *A61B 2017/0445* (2013.01); *A61B 2017/0456* (2013.01); *A61B 2017/0462* (2013.01);
(Continued)

(58) Field of Classification Search
CPC ............ A61B 17/0401; A61B 17/0487; A61B 17/0488; A61B 17/06166
See application file for complete search history.

(56) References Cited

U.S. PATENT DOCUMENTS

| | | | | |
|---|---|---|---|---|
| 992,821 | A | 5/1911 | Stewart | |
| 3,952,377 | A * | 4/1976 | Morell | E04C 5/122 403/374.2 |

(Continued)

FOREIGN PATENT DOCUMENTS

| | | | |
|---|---|---|---|
| CA | 3043526 | A1 | 5/2018 |
| CN | 101327131 | A | 12/2008 |

(Continued)

OTHER PUBLICATIONS

International Search Report and Written Opinion for International Application No. PCT/US2024/012769 dated Apr. 22, 2024.

(Continued)

*Primary Examiner* — Darwin P Erezo
*Assistant Examiner* — Christina C Lauer
(74) *Attorney, Agent, or Firm* — Carlson, Gaskey & Olds, P.C.

(57) ABSTRACT

Systems and methods are provided for performing tensionable knotless surgical procedures. A suture locking device that includes a one-way locking mechanism may be utilized for tensioning and locking one or more strands of suture during the surgical procedure. The one-way locking mechanism may be established by one or more locking barbs of the suture locking device.

20 Claims, 15 Drawing Sheets

(51) Int. Cl.
*A61B 17/00* (2006.01)
*A61F 2/00* (2006.01)

(52) U.S. Cl.
CPC ................. *A61B 2017/0488* (2013.01); *A61B 2017/0496* (2013.01); *A61F 2002/0081* (2013.01); *A61F 2002/0852* (2013.01); *A61F 2002/0882* (2013.01); *A61F 2002/0894* (2013.01); *A61F 2220/0033* (2013.01); *A61F 2220/0075* (2013.01); *A61F 2230/0052* (2013.01); *A61F 2250/0012* (2013.01)

(56) References Cited

U.S. PATENT DOCUMENTS 5,391,173 A 2/1995 Wilk
5,645,588 A 7/1997 Graf et al.
5,669,935 A 9/1997 Rosenman et al.
5,693,059 A 12/1997 Yoon
5,725,556 A 3/1998 Moser et al.
5,871,504 A 2/1999 Eaton et al.
5,935,149 A 8/1999 Ek
6,015,428 A 1/2000 Pagedas
6,066,160 A 5/2000 Colvin et al.
6,086,608 A 7/2000 Ek et al.
6,306,159 B1 10/2001 Schwartz et al.
6,554,862 B2 4/2003 Hays et al.
6,997,189 B2 2/2006 Biggs et al.
7,144,413 B2 12/2006 Wilford et al.
7,297,150 B2 11/2007 Cartledge et al.
7,799,073 B2 9/2010 Khalapyan
7,850,712 B2 12/2010 Conlon et al.
7,862,584 B2 1/2011 Lyons et al.
7,879,071 B2 2/2011 Carley et al.
7,883,538 B2 2/2011 To et al.
8,100,923 B2 1/2012 Paraschac et al.
8,109,968 B2 2/2012 Ashley et al.
8,202,295 B2 6/2012 Kaplan
8,231,626 B2 7/2012 Hulliger et al.
8,409,225 B2 4/2013 Bull et al.
8,419,769 B2 4/2013 Thal
8,523,902 B2 9/2013 Heaven et al.
8,652,173 B2 2/2014 Mansmann
8,709,040 B2 4/2014 Anderhub et al.
8,758,406 B2 6/2014 Fanton et al.
8,784,439 B1 7/2014 Ward et al.
8,870,877 B2 10/2014 Koogle, Jr.
8,915,943 B2 12/2014 Hunter
8,968,402 B2 3/2015 Myers et al.
9,078,645 B2 7/2015 Conklin et al.
9,265,494 B2 2/2016 Hester et al.
9,474,592 B1 * 10/2016 Vaughan ............... A61F 2/0811
9,801,719 B2 10/2017 Miraki
9,872,760 B2 1/2018 Lopez
10,076,322 B1 9/2018 Dreyfuss
D836,430 S 12/2018 Tillitski
10,143,506 B2 12/2018 Dreyfuss et al.
10,245,017 B2 4/2019 Stone
10,251,635 B2 4/2019 Khairkhahan et al.
10,258,400 B2 4/2019 Songer et al.
10,463,493 B2 11/2019 Miraki
10,828,146 B2 11/2020 Pilgeram et al.
10,952,781 B2 3/2021 Kobayashi
11,103,232 B2 8/2021 Kim
11,219,523 B2 1/2022 Miraki
11,395,737 B2 7/2022 Barajas-Torres et al.
11,737,877 B2 8/2023 Zhang et al.
11,857,232 B2 1/2024 Weiner et al.
12,011,055 B1 6/2024 Rowden
12,011,155 B2 6/2024 Sengun et al.
2003/0009196 A1 1/2003 Peterson
2004/0039404 A1 2/2004 Dreyfuss
2004/0260298 A1 12/2004 Kaiser et al.
2005/0216042 A1 9/2005 Gertner
2005/0245932 A1 11/2005 Fanton et al.
2005/0251208 A1 11/2005 Elmer et al.
2006/0058844 A1 3/2006 White et al.
2006/0241694 A1 10/2006 Cerundolo
2007/0123988 A1 5/2007 Coughlin
2008/0294177 A1 11/2008 To et al.
2009/0069846 A1 3/2009 Bull et al.
2009/0210005 A1 8/2009 Dinger, III et al.
2009/0281563 A1 11/2009 Newell et al.
2009/0292321 A1 11/2009 Collette
2010/0292733 A1 * 11/2010 Hendricksen ...... A61B 17/0401
606/232
2011/0208198 A1 8/2011 Anderson et al.
2012/0101526 A1 4/2012 Bennett
2013/0327679 A1 * 12/2013 Holt ..................... A61B 17/683
422/1
2014/0031864 A1 1/2014 Jafari et al.
2014/0074158 A1 3/2014 Feezor et al.
2014/0288595 A1 9/2014 Pandya
2016/0089131 A1 3/2016 Wade
2016/0220347 A1 8/2016 Hoover et al.
2017/0265917 A1 9/2017 Dreyfuss et al.
2018/0125472 A1 5/2018 Dreyfuss
2018/0221022 A1 8/2018 Choe et al.
2018/0249998 A1 9/2018 Chavan et al.
2019/0076141 A1 3/2019 Liu
2019/0117210 A1 4/2019 Fleischman et al.
2019/0134269 A1 5/2019 Murray et al.
2020/0306033 A1 10/2020 White et al.
2021/0000464 A1 1/2021 Zhang et al.
2021/0338300 A1 11/2021 Cole et al.
2022/0125427 A1 4/2022 Zhang et al.
2022/0133477 A1 5/2022 Miraki
2022/0142778 A1 5/2022 Skarsgard
2022/0323200 A1 10/2022 Connor et al.
2023/0107886 A1 4/2023 Yost et al.
2023/0218326 A1 7/2023 Golden et al.
2023/0263559 A1 8/2023 Heger et al.
2023/0310031 A1 10/2023 House et al.

FOREIGN PATENT DOCUMENTS

CN 106572909 B 10/2018
EP 3302301 B1 5/2020
EP 4103082 A1 12/2022
WO 9730649 A1 8/1997
WO 2015006739 A1 1/2015
WO 2016164588 A1 10/2016
WO 2017087848 A1 5/2017
WO 2019035944 A1 2/2019
WO 2020146471 A1 7/2020
WO 2022055838 A1 3/2022
WO 2024033836 A1 2/2024

OTHER PUBLICATIONS

International Search Report and Written Opinion for International Application No. PCT/US2024/012772 dated Jun. 26, 2024.
International Search Report and Written Opinion for International Application No. PCTUS2024038664 dated Oct. 30, 2024.
International Search Report and Written Opinion for International Application No. PCTUS2024038668 dated Oct. 28, 2024.
International Search Report and Written Opinion for International Application No. PCTUS2024038676 dated Dec. 16, 2024.
International Search Report and Written Opinion for International Application No. PCTUS2024038680 dated Jan. 2, 2025.
International Search Report and Written Opinion for International Application No. PCTUS2024038684 dated Dec. 23, 2024.
International Search Report and Written Opinion for International Application No. PCTUS2024038687 dated Oct. 30, 2024.
International Search Report and Written Opinion for International Application No. PCTUS2024039225 dated Nov. 14, 2024.
International Search Report and Written Opinion for International Application No. PCT/US2024/038969 dated Oct. 11, 2024.
International Search Report and Written Opinion for International Application No. PCT/US2024/039083 dated Oct. 17, 2024.
Partial Search PCTUS2024038676 Oct. 25, 2024.
Partial Search PCTUS2024038680 dated Oct. 30, 2024.

(56) References Cited

OTHER PUBLICATIONS

Partial Search PCTUS2024038684 Oct. 30, 2024.
GraftLink® ACL Reconstruction With ACL TightRope® II Implant for InternalBrace™ Technique, Arthrex GmbH, 2021.
International Preliminary Report on Patentability PCT/US2024/012769 dated Aug. 7, 2025.
International Preliminary Report on Patentability PCT/US2024/012772 dated Aug. 7, 2025.

* cited by examiner

SUTURE ANCHORS WITH ONE-WAY LOCKING MECHANISMS

CROSS-REFERENCE TO RELATED APPLICATIONS

This application claims the benefit of U.S. Provisional Application No. 63/620,280, which was filed on Jan. 12, 2024 and is incorporated herein by reference in its entirety.

BACKGROUND

This disclosure relates to the field of surgery, and more particularly to various surgical locking devices that are capable of locking suture when performing a variety of tensionable knotless surgical procedures.

Repetitive trauma to a joint, such as a knee, ankle, hip, elbow, or shoulder joint, for example, may result in the development of tissue defects (e.g., soft tissue tears, cartilage defects, etc.). If not treated, tissue defects could further deteriorate, thereby causing joint instability and discomfort.

SUMMARY

This disclosure relates to systems and methods for performing tensionable knotless surgical procedures, such as tissue repairs or reconstructions, for example. Surgical locking devices that include a one-way locking mechanism may be utilized when performing the tensionable knotless surgical procedures for tensioning and locking one or more strands of suture.

An exemplary suture locking device may include, inter alia, a suture anchor including an internal bore, and a locking ferrule positioned within the internal bore and including a one-way locking mechanism configured for locking a suture relative to the suture anchor.

An exemplary surgical method may include, inter alia, inserting a suture anchor into a bone, passing a suture through or around a tissue, shuttling the suture through a cannulation of a locking ferrule, and tensioning the suture in a first direction relative to the cannulation to knotlessly secure the tissue at a desired position relative to the bone.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
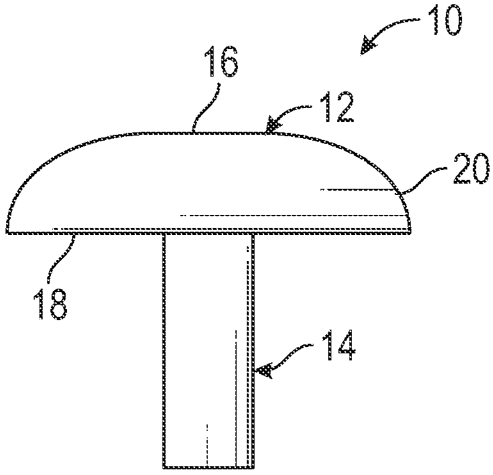
FIG. 1 illustrates a locking ferrule that can be used for performing various tensionable knotless surgical procedures.
Figure 2:
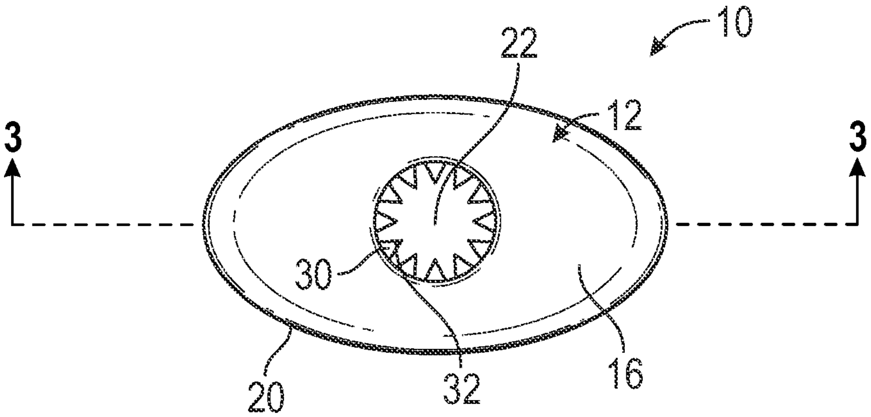
FIG. 2 is a top view of the locking ferrule of FIG. 1.
Figure 3:
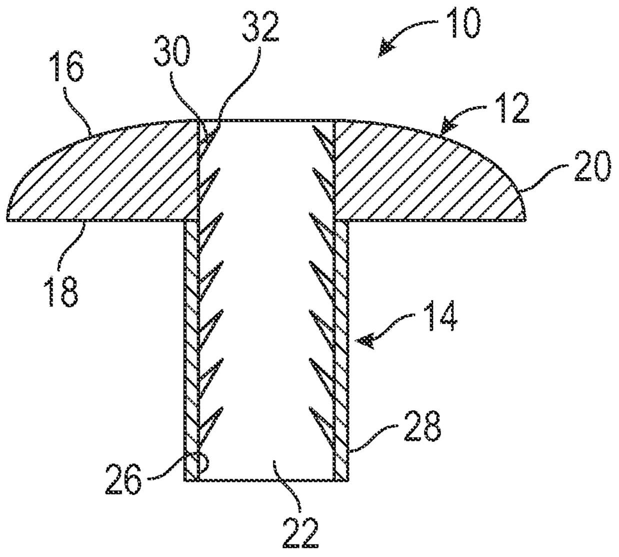
FIG. 3 is a cross-sectional view through section 3-3 of FIG. 2.
Figure 4A:
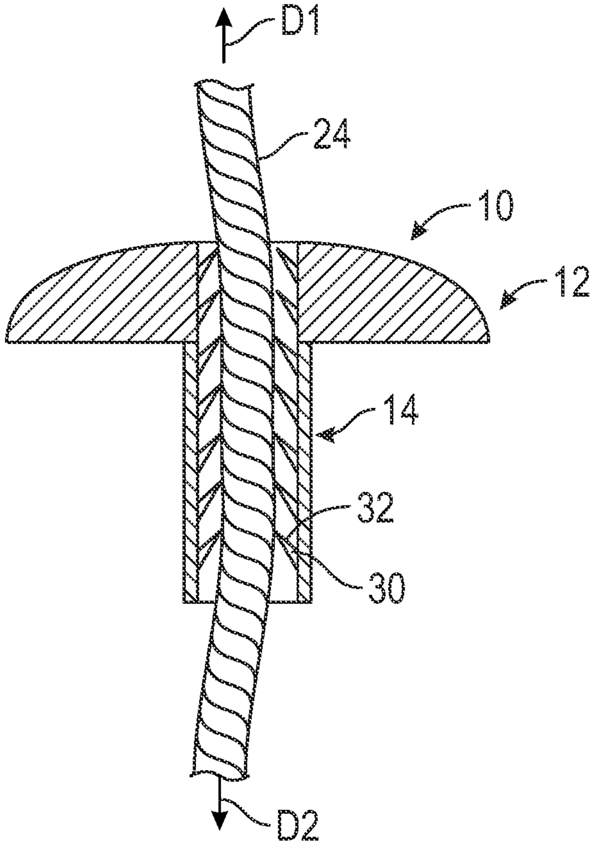
FIG. 4A schematically illustrates locking a suture relative to the locking ferrule of FIGS. 1-3.
Figure 4B:
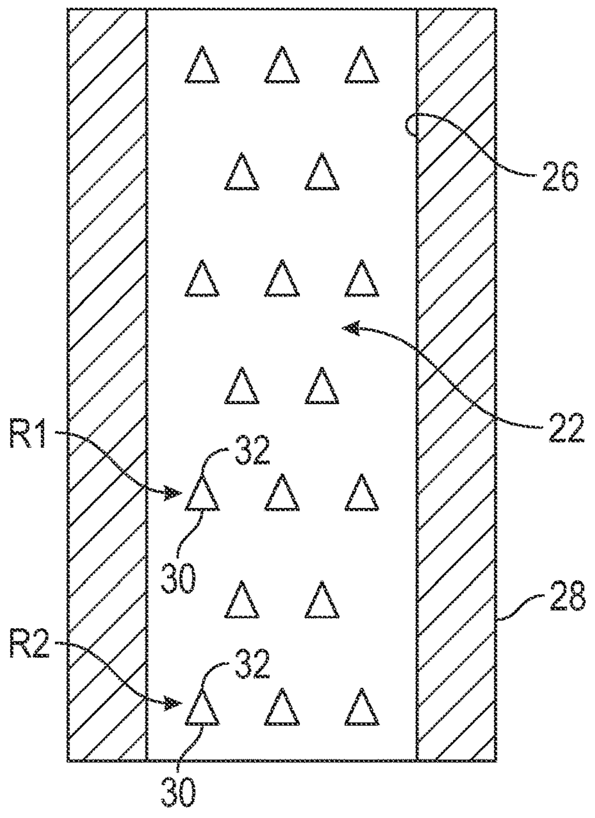
FIG. 4B illustrates a plurality of rows of locking barbs of the locking ferrule of FIG. 1.
Figure 4C:
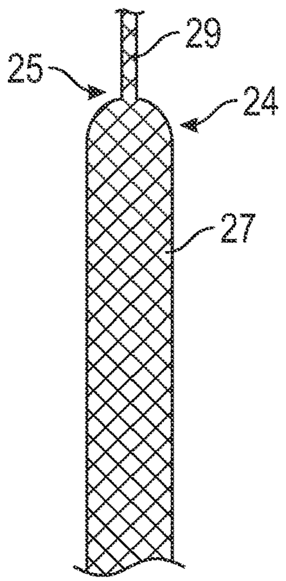
FIG. 4C illustrates a suture having a varying thickness.

This disclosure relates to systems and methods for performing tensionable knotless surgical procedures. A locking ferrule or other suture locking device that includes a one-way locking mechanism may be utilized as part of the tensionable knotless repairs for tensioning and locking one or more strands of suture. These and other features of this disclosure are described in further detail below.

An exemplary suture locking device may include, inter alia, a suture anchor including an internal bore, and a locking ferrule positioned within the internal bore and including a one-way locking mechanism configured for locking a suture relative to the suture anchor.

In any further embodiment, the one-way locking mechanism is configured to allow the suture to be tensioned in a first direction and prevent the suture from moving in a second direction.

In any further embodiment, the one-way locking mechanism is established by a plurality of locking barbs provided within a cannulation of the locking ferrule.

In any further embodiment, the cannulation extends through a tubular body of the locking ferrule.

In any further embodiment, the plurality of locking barbs are each angled in a common direction within the cannulation.

In any further embodiment, the plurality of locking barbs are arranged in at least a first row and a second row along the cannulation.

In any further embodiment, a first portion of the plurality of locking barbs of the first row are staggered relative to second portion of the plurality of locking barbs of the second row.

In any further embodiment, the locking ferrule includes a second plurality of barbs provided at an outer diameter wall of the locking ferrule.

In any further embodiment, the internal bore extends through a sheath of the suture anchor.

In any further embodiment, the sheath is a soft body made exclusively of soft, suture-based materials.

In any further embodiment, an outer diameter wall of the locking ferrule includes a second plurality of barbs that are configured to engage an internal wall of the sheath.

In any further embodiment, a shuttle device is received through the sheath and is configured to shuttle the suture through the sheath and the locking ferrule.

In any further embodiment, the suture includes a varying thickness.

In any further embodiment, the suture includes at least one tapered region where the suture transitions between a thickened section and a thinned section.

An exemplary surgical method may include, inter alia, inserting a suture anchor into a bone, passing a suture through or around a tissue, shuttling the suture through a cannulation of a locking ferrule, and tensioning the suture in a first direction relative to the cannulation to knotlessly secure the tissue at a desired position relative to the bone.

In any further embodiment, the surgical method includes locking the suture within the cannulation to prevent movement of the suture in a second direction relative to the cannulation.

In any further embodiment, the locking ferrule includes a plurality of locking barbs positioned within the cannulation and arranged to allow the suture to be tensioned in the first direction but prevent movement of the suture in a second direction.

In any further embodiment, the locking ferrule includes a second plurality of locking barbs positioned on an outer diameter wall of the locking ferrule.

In any further embodiment, the tissue is a ligament, a tendon, or a muscle.

In any further embodiment, the locking ferrule is positioned within an internal bore of a sheath of the suture anchor.

FIGS. 1-4C illustrate an exemplary locking ferrule 10 that can be used when performing various tensionable knotless surgical procedures. For example, the locking ferrule 10 could be utilized during surgical methods for attaching tissue (e.g., ligament, tendon, graft, etc.) to bone or for repairing any other type of tissue effect. The locking ferrule 10 could be used in conjunction with a variety of orthopedic surgical repairs or reconstructions, including but not limited to ulnar collateral ligament repairs, AC joint repairs, rotator cuff repairs, Achilles tendon repairs, patellar tendon repairs, and biceps tendon repairs, among many others.

The locking ferrule 10 is an exemplary suture locking device that can include a cap portion 12 and a barrel portion 14 that protrudes from the cap portion 12. The cap portion 12 and the barrel portion 14 may be formed together as part of a unitary structure of the locking ferrule 10. In an embodiment, the cap portion 12 and the barrel portion 14 are arranged to provide a top hat-like appearance of the locking ferrule 10. However, the specific size, shape, and material make-up of the locking ferrule 10 are not intended to limit this disclosure.

The cap portion 12 of the locking ferrule 10 may include a top surface 16, a bottom surface 18, and a side wall 20 that extends between the top surface 16 and the bottom surface 18. The bottom surface 18 may include a slightly concave curvature for conforming to the contour of a bone. The barrel portion 14 may protrude outwardly from the bottom surface 18 of the cap portion 12. As further detailed below, the locking ferrule 10 may be positioned relative to a bone such that the barrel portion 14 is accommodated within a socket or tunnel formed in the bone and the cap portion 12 is seated relative to the cortex of the bone. In the seated position, the top surface 16 of the cap portion 12 faces away from the bone and the bottom surface 18 faces toward the bone.

A cannulation 22 may extend through the cap portion 12 and the barrel portion 14. The cannulation 22 may establish an internal passageway for accommodating one or more strands of suture 24 (see FIG. 4A) or other structures (e.g., wires, shafts, etc.). The locking ferrule 10 of this embodiment may therefore provide a "single-chamber" design.

The cannulation 22 may be circumscribed by an interior wall 26 of the locking ferrule 10. The interior wall 26 may be established by both the cap portion 12 and the barrel portion 14. The cannulation 22 may be straight or may taper in a direction toward a distal tip of the barrel portion 14. An outer diameter wall 28 of the barrel portion 14 may be smooth or could alternatively include threads, barbs, or other features for facilitating bone fixation.

A plurality of locking barbs 30 may protrude inwardly from the interior wall 26. The locking barbs 30 may therefore occupy at least a portion of the open space of the cannulation 22. In an embodiment, the locking barbs 30 are integrally formed (e.g., molded) features of the body of the locking ferrule 10. The locking barbs 30 may be provided along an entire length of the cannulation 22 or at only select portions thereof. The locking barbs 30 may be either rigid or flexible structures.

The locking barbs 30 may be arranged in multiple rows along the length of the cannulation 22. For example, the locking barbs 30 may be arranged in a least a first row R1 and a second row R2 (see FIG. 4B). In an embodiment, the locking barbs 30 of the second row R2 are staggered relative to the locking barbs 30 of the first row R1 (see FIG. 4B).

Each locking barb 30 may include a sharp or pointed tip 32, and, in this implementation, each locking barb 30 may be angled in a direction toward the cap portion 12. The locking barbs 30 may therefore establish a one-way locking mechanism that permits one or more sutures 24 to pass through the cannulation 22 in a first direction D1 while preventing the suture(s) 24 from being tensioned or otherwise moved in a second direction D2. The staggered relationship of the rows of locking barbs 30 can maximize engagement with the suture 24 once it is passed through the cannulation 22.

The suture 24 may be FiberWire®, FiberTape®, or any other suitable suture product. FiberWire® and FiberTape® are suture products marketed and sold by Arthrex, Inc. However, other suture products could be utilized for the suture 24 within the scope of this disclosure. The size and type of suture utilized in conjunction with the locking ferrule 10 are not intended to limit this disclosure.

The suture 24 may include a varying thickness. The suture 24 may therefore include one or more tapered regions 25 where the suture 24 transitions between a thickened section 27 and a thinned section 29 (see, e.g., FIG. 4C). The thinned sections 29 can facilitate passing the suture 24 through the cannulation 22, such as via a suitable suture loader that can be provided as part of a suture locking system that includes the locking ferrule 10, for example, and the thickened sections 27 can provide greater surface area for the locking barbs 30 to engage in order to sufficiently lock the suture 24 relative to the locking ferrule 10.

In an embodiment, the thickened sections 27 of the suture 24 are about twice as thick as the thinned sections 29. However, other ratios (e.g., 1.5:1, 3:1, etc.) between the relative thicknesses (e.g., outer diameters) of the thickened sections 27 and the thinned sections 29 are contemplated within the scope of this disclosure.

Figure 5:
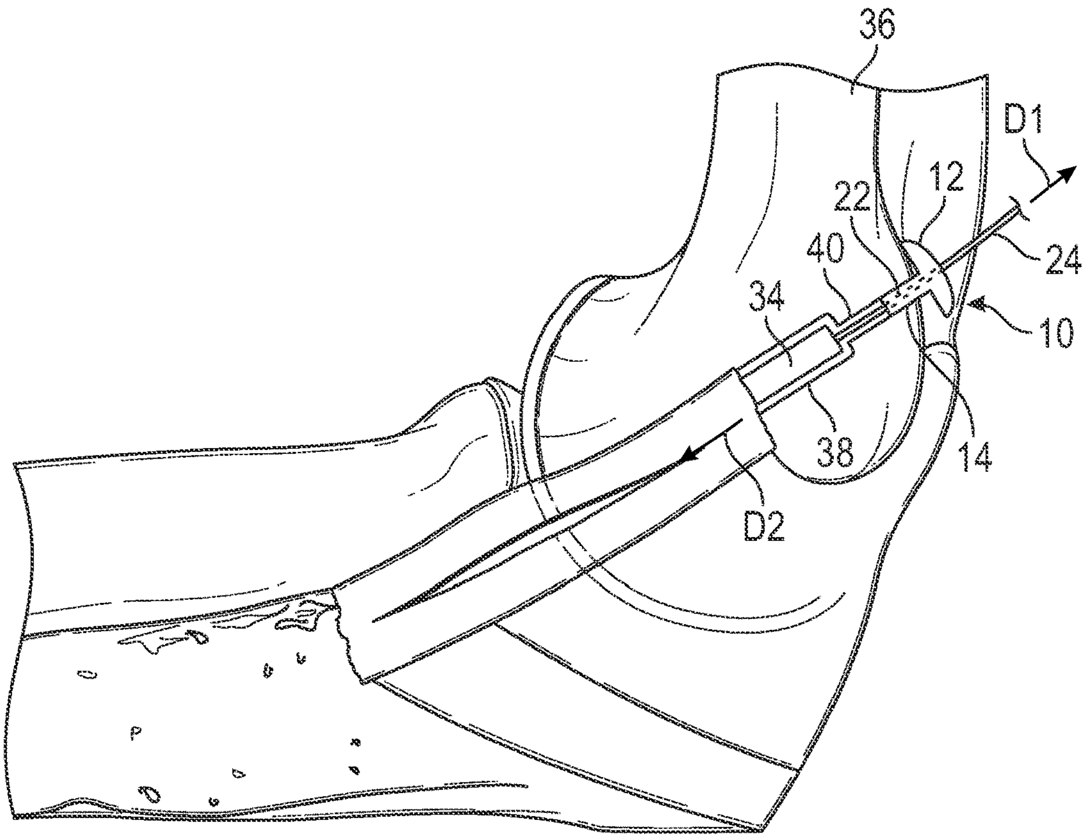
FIG. 5 schematically illustrates a surgical method for performing a tissue repair.

FIG. 5 schematically illustrates an exemplary surgical method in which the locking ferrule 10 of FIGS. 1-4 may be utilized to tension and lock suture 24 during a surgical repair. In this embodiment, the surgical method may involve securing a graft 34 (e.g., a harvested muscle, tendon, or ligament) to a bone 36 (e.g., a humerus), such as part of an ulnar collateral ligament (UCL) reconstruction, for example.

The surgical method may include preparing a socket 38 in the bone 36. The socket 38 may be sized for receiving a portion of the graft 34. One or more sutures 24 may be attached to the graft 34 and can be used to pull or otherwise position the graft 34 within the socket 38. The suture 24 may be passed through the cannulation 22 of the locking ferrule 10 either before or after inserting the barrel portion 14 of the locking ferrule into a passage 40 of the bone 36 that is connected to the socket 38.

At this point of the surgical method, the graft 34 may be reduced into place within the socket 38. The suture 24 may subsequently be tensioned and locked in place by the locking ferrule 10. For example, after loading the suture 24 through the cannulation 22 of the locking ferrule 10, the suture 24 may be tensioned in the direction D1 to allow the pointed tips 32 of the locking barbs 30 to interdigitate with the section of the suture 24 accommodated within the cannulation 22, thereby locking the suture 24 in place and preventing it from sliding back in the second direction D2. The graft 34 can therefore be securely tensioned and fixated within the socket 38 of the bone 36.

Figure 6:
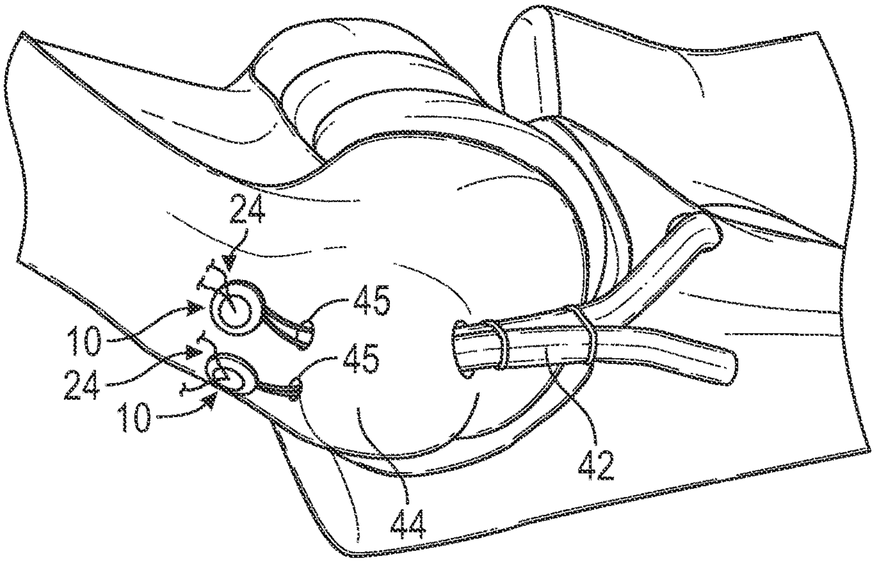
FIG. 6 schematically illustrates another exemplary surgical method for performing a tissue repair.

In the above surgical method, a single locking ferrule 10 is used to tension and lock the suture 24. However, other surgical methods, such as a docking technique for performing an UCL repair, for example, may involve the use of multiple locking ferrules 10 for securing a graft 42 relative to a bone 44 (see FIG. 6). One locking ferrule 10 may inserted into each bone tunnel 45 that is formed in the bone 44 as part of the docking technique.

Figure 7:
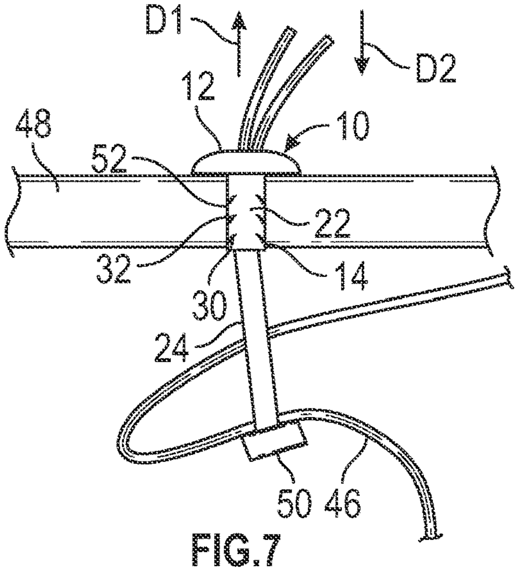
FIG. 7 schematically illustrates yet another exemplary surgical method for performing a tissue repair.
Figure 8:
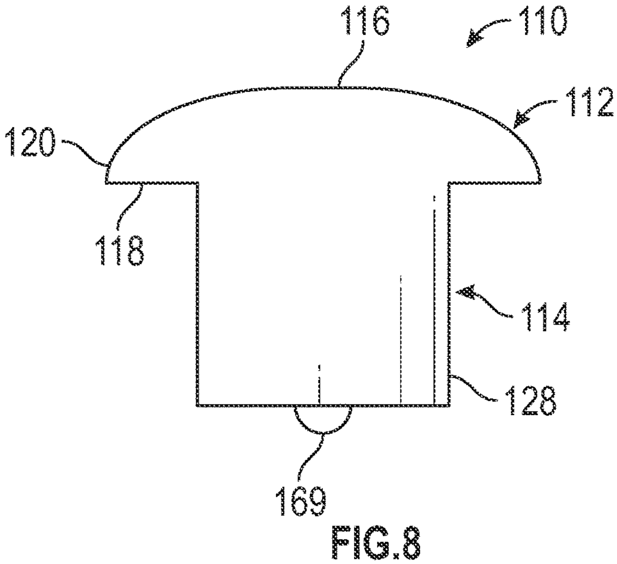
FIG. 8 illustrates another exemplary locking ferrule that can be used for performing various tensionable knotless surgical procedures.
Figure 9:
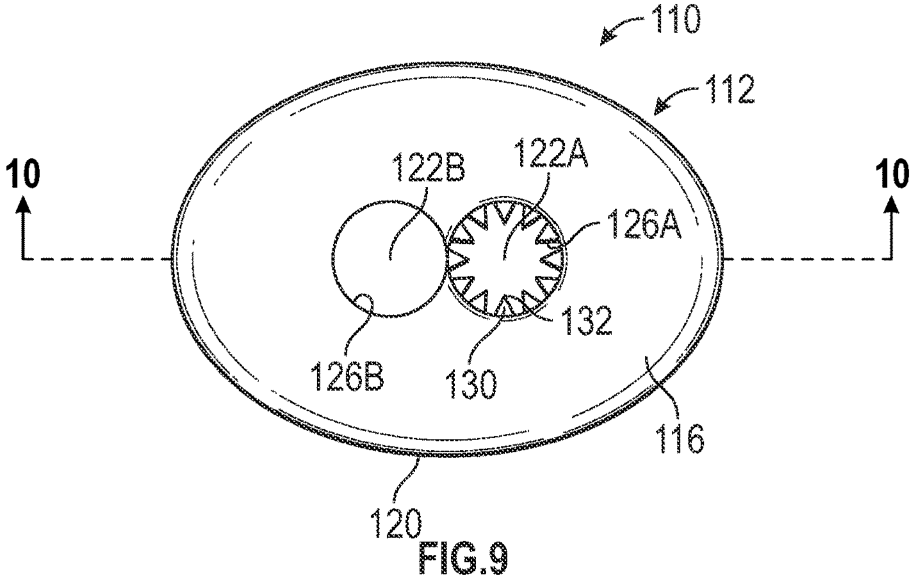
FIG. 9 is a top view of the locking ferrule of FIG. 8.

FIG. 7 schematically illustrates another exemplary surgical method in which the locking ferrule 10 of FIGS. 1-4 may be utilized to tension and lock suture 24 during a surgical procedure. In this embodiment, the surgical method may involve securing suture 24 to a first bone 46 (e.g., a coracoid) and a second bone 48 (e.g., a clavicle), such as part of an acromioclavicular (AC) joint repair, for example.

The suture 24 may be secured relative to the first bone 46 by a button 50. The suture 24 may subsequently be tensioned and locked in place relative to the second bone 48 using the locking ferrule 10. For example, after loading the suture 24 through the cannulation 22 of the locking ferrule 10, the suture 24 may be tensioned in the direction D1 to allow the pointed tips 32 of the locking barbs 30 to interdigitate with the section of the suture 24 accommodated within the cannulation 22, thereby locking the suture 24 in place and preventing it from sliding back toward the second direction D2. The suture 24 may be passed through the cannulation 22 of the locking ferrule 10 either before or after inserting the barrel portion 14 of the locking ferrule 10 into a passage 52 formed in the second bone 48. The suture 24 may tensioned until the second bone 48 is located at a desired position relative to the first bone 46.

FIGS. 8-11 illustrate another exemplary locking ferrule 110 that can be used when performing various tensionable knotless surgical procedures. The locking ferrule 110 is similar to the locking ferrule 10 described above and includes a cap portion 112 and a barrel portion 114 that protrudes from the cap portion 112. The cap portion 112 and the barrel portion 114 may be formed together as part of a unitary structure of the locking ferrule 110. In an embodiment, the cap portion 112 and the barrel portion 114 are arranged to provide a top hat-like appearance of the locking ferrule 110. However, the specific size, shape, and material make-up of the locking ferrule 110 are not intended to limit this disclosure.

The cap portion 112 of the locking ferrule 110 may include a top surface 116, a bottom surface 118, and a side wall 120 that extends between the top surface 116 and the bottom surface 118. The bottom surface 118 may include a slightly concave curvature for conforming to the contour of a bone. The barrel portion 114 may protrude outwardly from the bottom surface 118 of the cap portion 112. An outer diameter wall 128 of the barrel portion 114 may be smooth or could alternatively include threads, barbs, or other features for facilitating bone fixation.

A first cannulation 122A and a second cannulation 122B may extend through the cap portion 112 and the barrel portion 114. The first and second cannulations 122A, 122B may establish internal passageways for accommodating one or more strands of suture 124 (see, e.g., FIGS. 10 and 11) through the locking ferrule 110. The locking ferrule 110 of this embodiment may therefore provide a “dual-chamber” design.

A dividing wall 154 may separate the first cannulation 122A and the second cannulation 122B from one another. The dividing wall 154 may be established by both the cap portion 112 and the barrel portion 114 of the locking ferrule 110.

The first cannulation 122A may include a plurality of locking barbs 130. The locking barbs 130 may protrude inwardly from an interior wall 126A that circumscribes the first cannulation 122A. The locking barbs 130 may therefore occupy at least a portion of the open space of the first cannulation 122A. In an embodiment, the locking barbs 130 are integrally formed (e.g., molded) features of the body of the locking ferrule 110. The locking barbs 130 may be provided along an entire length of the cannulation 122A or at only select portions thereof. Each locking barb 130 may include a sharp or pointed tip 132, and, in an exemplary implementation, each locking barb 130 may be angled in a direction toward the cap portion 112. The locking barbs 130 may establish a one-way locking mechanism that permits one or more sutures 124 (see FIG. 10) to be passed through the first cannulation 122A in a first direction D1 while preventing the suture(s) 24 from being tensioned or otherwise moved in a second direction D2.

The second cannulation 122B may be circumscribed by an interior wall 126B. The second cannulation 122B may exclude locking barbs, and therefore the interior wall 126B can provide a substantially smooth surface that allows one or more sutures 124 to be shuttled through the locking ferrule 110 prior to being locked in place via the locking barbs 130 of the first cannulation 122A.

Figure 10:
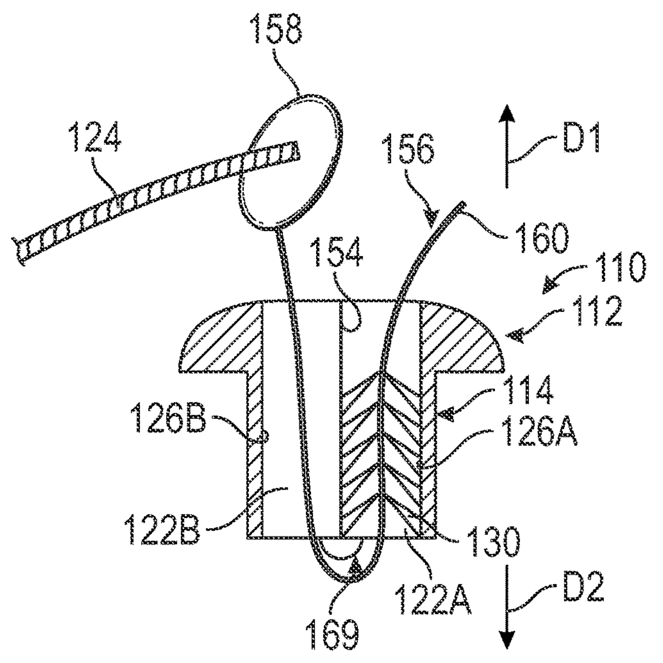
FIG. 10 illustrates the locking ferrule of FIGS. 8 and 9 with a shuttle device.

As shown in FIG. 10, the one or more sutures 24 may be shuttled through the second cannulation 122B and then through the first cannulation 122A of the locking ferrule 110 using a shuttle device 156. The shuttle device 156 may be a passing wire or another suture, for example. The one or more sutures 124 may be passed through an eyelet 158 of the shuttle device 156, and a free end 160 of the shuttle device 156 may then be pulled (in the first direction D1) to pass the suture 124 through the locking ferrule 110.

Figure 11:
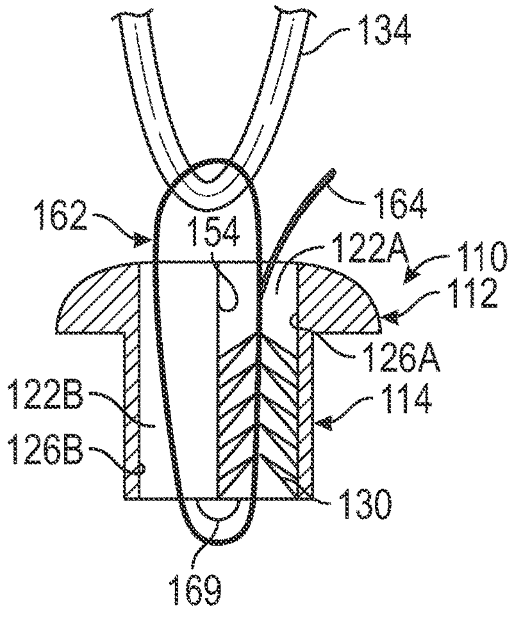
FIG. 11 illustrates the locking ferrule of FIGS. 8 and 9 with an adjustable loop.

Alternatively, as shown in FIG. 11, an adjustable spliced loop 162 may be pre-attached to the locking ferrule 110 via the first and second cannulations 122A, 122B. A graft 134 or other component may be looped through and/or around the adjustable spliced loop 162. A tensioning strand 164 of the adjustable spliced loop 162 may then be tensioned to reduce the size of the adjustable spliced loop 162 and thereby move the graft 134 into a desired position relative to the locking ferrule 110. The locking barbs 130 of the first cannulation 122A can lock the reduced position of the adjustable spliced loop 162 (and thus the graft 134) when tension is released on the tensioning strand 164.

A post 169 may protrude from a distal end of the barrel portion 114 at a location between the first cannulation 122A and the second cannulation 122B. The post 169 may be curved to provide a smooth surface for suture 124 to glide over as it is being shuttled through the locking ferrule 110.

Figure 12:
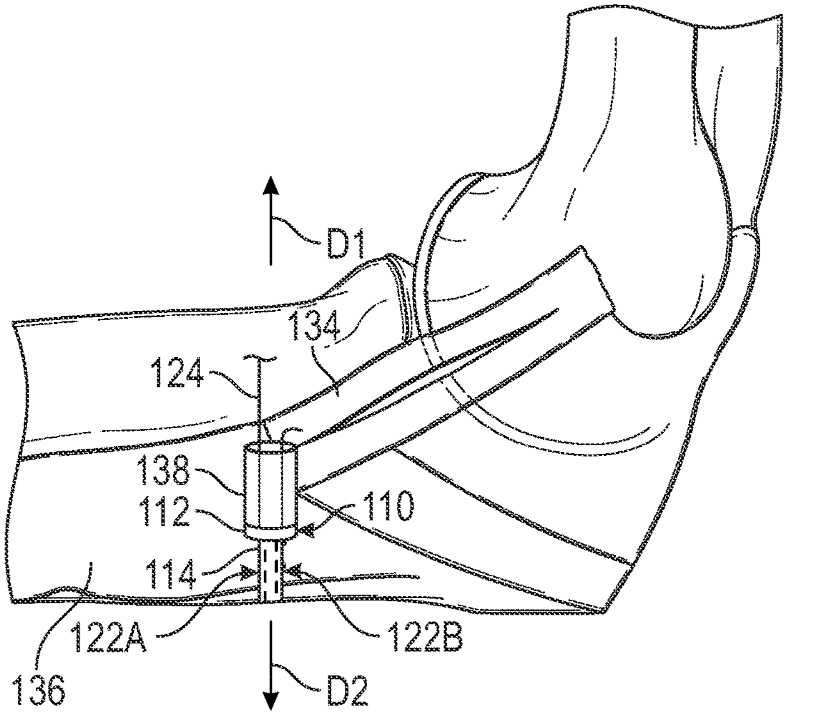
FIG. 12 schematically illustrates another exemplary surgical method for performing a tissue repair.
Figure 13:
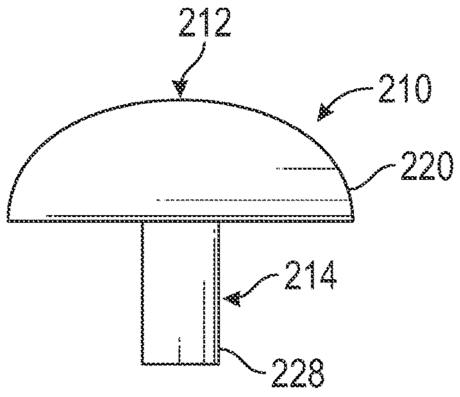
FIG. 13 illustrates another exemplary locking ferrule that can be used for performing various tensionable knotless surgical procedures.

The locking ferrule 110 described above and shown in FIGS. 8-11 may be utilized to tension and knotlessly fixate one or more sutures 124 as part of various surgical methods. FIG. 12 schematically illustrates one such surgical method for securing a graft 134 (e.g., a harvested muscle, tendon, or ligament) to a bone 136 (e.g., an ulna), such as part of an ulnar collateral ligament (UCL) reconstruction, for example.

The surgical method may include preparing a socket 138 in the bone 136. The locking ferrule 110 may be inserted into the bottom of the socket 138 either before or after connecting the suture 124 that is attached to the graft 134 to the locking ferrule 110.

At this point of the surgical method, the graft 134 may be reduced into place relative to the socket 138. The suture 124 may subsequently be tensioned and locked in place using the locking ferrule 110. For example, after loading the suture 124 through the first and second cannulations 122A, 122B of the locking ferrule 110, the suture 124 may be tensioned in the direction D1 to allow the pointed tips 132 of the locking barbs 130 to interdigitate with the section of the suture 124 accommodated within the first cannulation 122A, thereby locking the suture 124 in place and preventing it from sliding in the second direction D2.

FIGS. 13-17 illustrate another exemplary locking ferrule 210 that can be used when performing various tensionable knotless surgical procedures. The locking ferrule 210 is similar to the locking ferrule 10 described above may include a cap portion 212 and a barrel portion 214 that protrudes from the cap portion 212. A cannulation 222 may extend through the cap portion 212 and the barrel portion 214 for establishing an internal passageway for accommodating one or more strands of suture 224, for example.

The cannulation 222 may be circumscribed by an interior wall 226 of the locking ferrule 210. An outer diameter wall 228 of the barrel portion 214 may be smooth or could alternatively include threads, barbs, or other features for facilitating bone fixation.

A plurality of locking barbs 230 may protrude inwardly from the interior wall 226. The locking barbs 230 may therefore occupy at least a portion of the open space of the cannulation 222. The locking barbs 230 may establish a one-way locking mechanism that permits suture 224 to pass through the cannulation 222 in a first direction while preventing the suture(s) from being tensioned or otherwise moved in a second direction.

One or more slots 266 may be formed in the cap portion 212. Each slot 266 may open into the cannulation 222. Each slot 266 may function as a cleat for locking the suture 224 relative to the locking ferrule 210. The size and shape of the slots 266 is not intended to limit this disclosure as is evident from the exemplary design options illustrated in FIGS. 14, 15, and 16.

Figure 14:
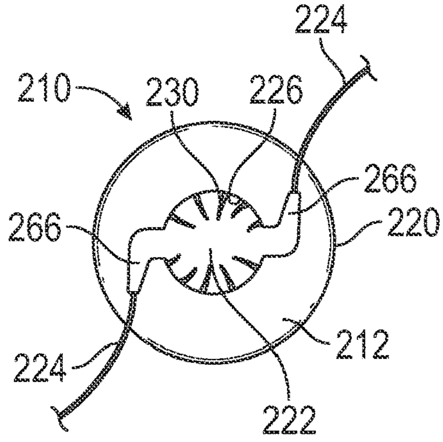
FIG. 14 is a top view of the locking ferrule of FIG. 13.
Figure 15:
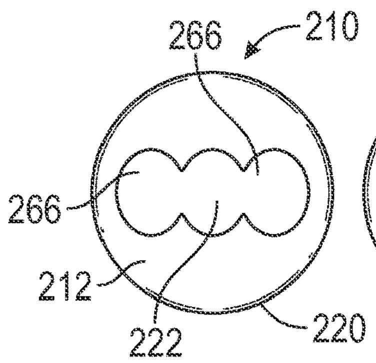
FIG. 15 illustrates an exemplary slot of a locking ferrule.
Figure 16:
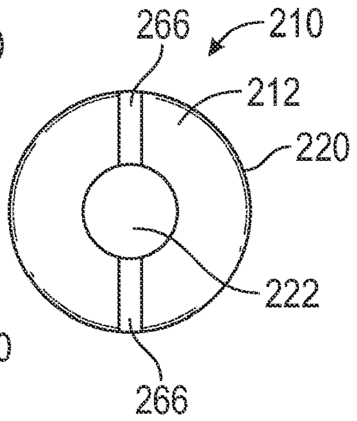
FIG. 16 illustrates another exemplary slot of a locking ferrule.

In an embodiment, the slots 266 do not extend through a side wall 220 of the cap portion 212 (see FIGS. 14 and 15). In another embodiment, the slots 266 extend through the side wall 220 of the cap portion 212 for facilitating suture loading into the cannulation 222 (see FIG. 16).

Figure 17:
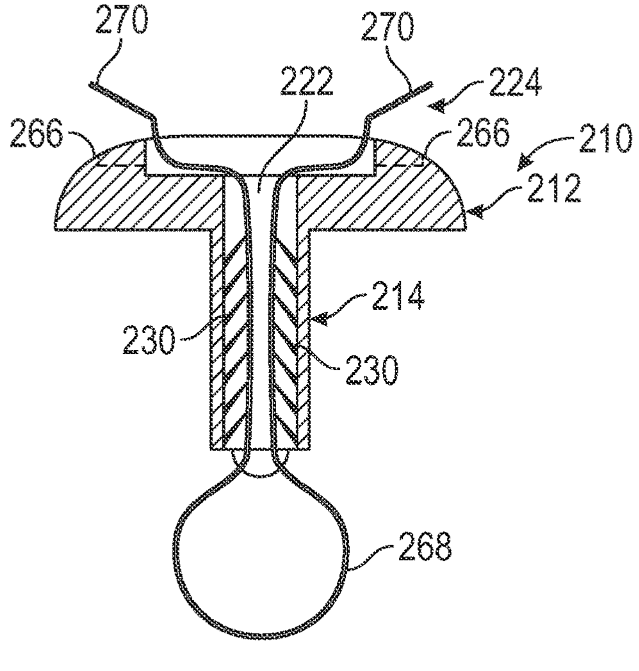
FIG. 17 schematically illustrates a suture passed through the locking ferrule of FIGS. 13 and 14 and arranged to provide a loop.

In an embodiment, suture 224 may be arranged within the cannulation 222 in a manner that forms a loop 268 in the suture 224 (see, e.g., FIG. 17). The loop 268 can be used to suspend a graft within a bone tunnel, for example. Free ends 270 of the suture 224 may be cleated within the slots 266 to help force the portions of the suture 224 that are passed through the cannulation 222 into increased engagement with the locking barbs 230.

Figure 18:
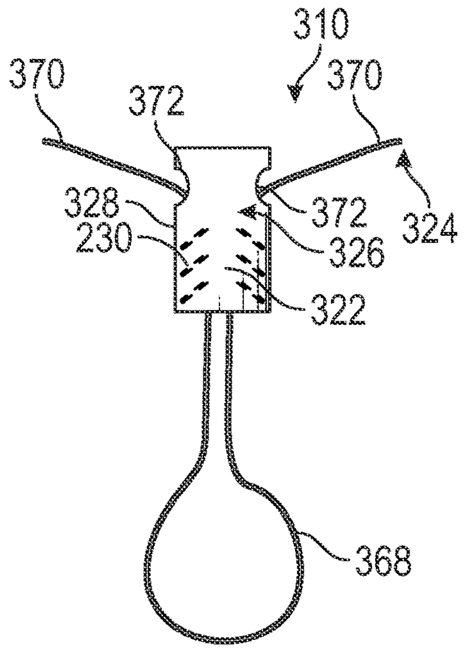
FIG. 18 illustrates another exemplary locking ferrule.

In the embodiments described above, the exemplary locking ferrules include both a cap portion and a barrel portion that are arranged together to provide a top hat-like appearance of the locking ferrule. However, other locking ferrule implementations could exclude the cap portion, and therefore locking ferules that do not exhibit a top hat-like appearance are also contemplated within the scope of this disclosure. For example, FIG. 18 illustrates an exemplary locking ferrule 310 that includes a barrel portion 314 without an integrated cap portion. The barrel portion 314 may be tubular shaped and may be constructed from either metallic materials or plastic materials. However, the specific size, shape, and material make-up of the barrel portion 314 are not intended to limit this disclosure.

A cannulation 322 may extend through the barrel portion 314 and may establish an internal passageway for accommodating one or more strands of suture 324. The cannulation 322 may be circumscribed by an interior wall 326 of the locking ferrule 310. An outer diameter wall 328 of the barrel portion 314 may be smooth or could alternatively include threads, barbs, or other features for facilitating bone fixation.

A plurality of locking barbs 330 may protrude inwardly from the interior wall 326. The locking barbs 330 may therefore occupy at least a portion of the open space of the cannulation 322. The locking barbs 330 may establish a one-way locking mechanism that permits one or more sutures 324 to pass through the cannulation 322 in a first direction while preventing the suture(s) from being tensioned or otherwise moved in a second direction.

One or more side openings 372 may be formed through the barrel portion 314. Each side opening 372 may open through both the interior wall 326 and the outer diameter wall 328. The side openings 372 are therefore connected to the cannulation 322.

In an embodiment, the suture 324 may be arranged within the cannulation 322 in a manner that forms a loop 368 in the suture 324. The loop 368 can be used to suspend a graft within a bone tunnel or fixate soft tissue or bone, for example. Free ends 370 of the suture 324 may be passed through each side opening 372 and then tensioned to help force the portions of the suture 324 that are passed through the cannulation 322 into increased engagement with the locking barbs 330.

Figure 19:
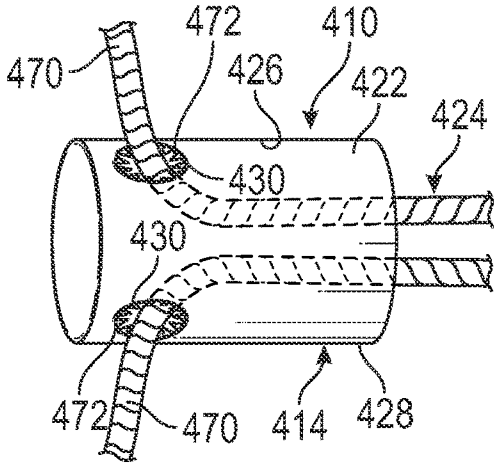
FIG. 19 illustrates another exemplary locking ferrule.

FIG. 19 illustrates another exemplary locking ferrule 410 that includes a barrel portion 414 without an integrated cap portion. A cannulation 422 may extend through the barrel portion 414 and may establish an internal passageway for accommodating one or more strands of suture 424. The cannulation 422 may be circumscribed by an interior wall 426 of the locking ferrule 410. An outer diameter wall 428 of the barrel portion 314 may be smooth or could alternatively include threads, barbs, or other features for facilitating bone fixation.

One or more side openings 472 may be formed through the barrel portion 414. Each side opening 472 may open through both the interior wall 426 and the outer diameter wall 428. The side openings 472 are therefore connected to the cannulation 422.

Each side opening 472 may include a plurality of locking barbs 430. The locking barbs 430 may establish a one-way locking mechanism that permits the suture 424 to pass through the side openings 472 in a first direction while preventing the suture(s) from being tensioned or otherwise moved in a second direction. Although not specifically shown in the exemplary embodiment, the cannulation 422 could be provided with additional locking barbs.

Figure 20:
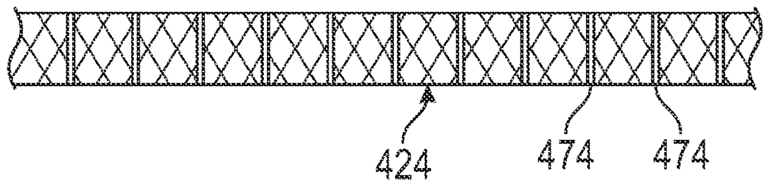
FIG. 20 illustrates a suture that includes partitions.

Free ends 470 of the suture 424 may be passed through each side opening 472 and then tensioned to lock the suture 424 in place relative to the locking ferrule 410. In an embodiment, the suture 424 may include a plurality of partitions 474 (see FIG. 20) that can interface with the locking barbs 430 of the side openings 472 to create a "rip-stop" effect as the free end 470 of the suture 424 is being tensioned.

Figure 21:
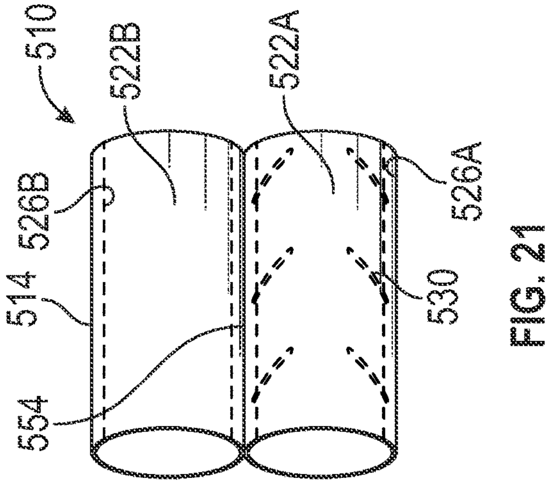
FIG. 21 illustrates another exemplary locking ferrule.
Figure 22:
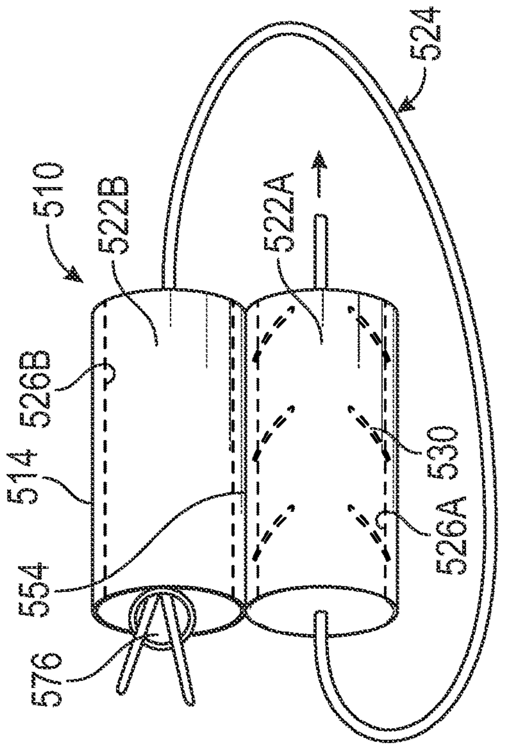
FIG. 22 schematically illustrates locking a suture relative to the locking ferrule of FIG. 21.

FIGS. 21 and 22 illustrate yet another exemplary locking ferrule 510 that includes a barrel portion 514 without an integrated cap portion. A first cannulation 522A and a second cannulation 522B may extend through the barrel portion 514. A dividing wall 554 may separate the first cannulation 522A and the second cannulation 522B from one another.

The first and second cannulations 522A, 522B may establish internal passageways for accommodating one or more strands of suture 524 (see FIG. 22) through the locking ferrule 510. The locking ferrule 510 of this embodiment therefore provides another "dual-chamber" design.

The first cannulation 522A may include a plurality of locking barbs 530. The locking barbs 530 may protrude inwardly from an interior wall 526A that circumscribes the first cannulation 522A. The locking barbs 530 may therefore occupy at least a portion of the open space of the first cannulation 522A. The locking barbs 530 may establish a one-way locking mechanism for locking suture 524 relative to the locking ferrule 510.

The second cannulation 522B may be circumscribed by an interior wall 526B. In an embodiment, the second cannulation 522B excludes locking barbs, and therefore the interior wall 526B can be configured to provide a substantially smooth surface that allows the suture 524 to be shuttled through the locking ferrule 510 prior to being locked in place via the locking barbs 530 of the first cannulation 522A. The suture 524 may be retained relative to the second cannulation 522B by a knot 576.

Figure 23:
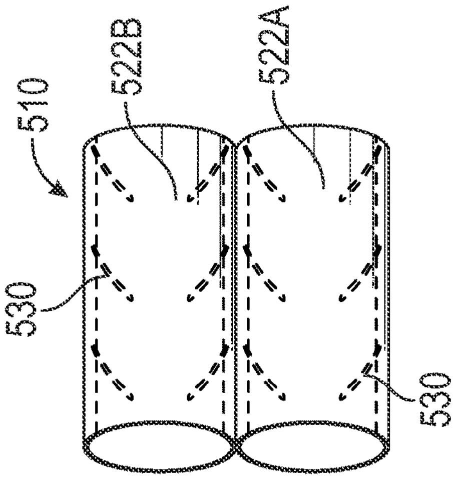
FIG. 23 illustrates another exemplary locking ferrule.
Figure 24:
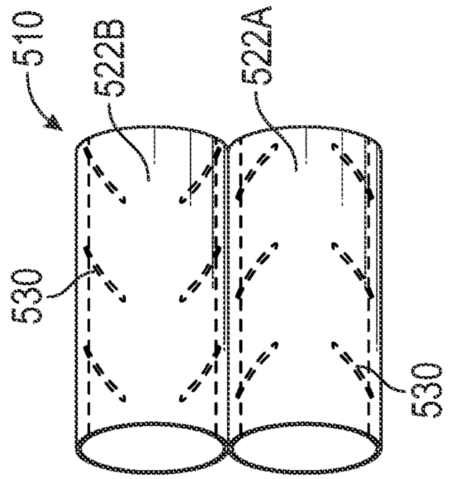
FIG. 24 illustrates another exemplary locking ferrule.

In another embodiment, the second cannulation 522B includes an additional plurality of locking barbs 530 (see FIGS. 23 and 24). If provided within the second cannulation 522B, the additional locking barbs 530 may be angled in the same direction (see FIG. 23) or in an opposite direction (see FIG. 24) as the locking barbs 530 of the first cannulation 522A.

Figure 25:
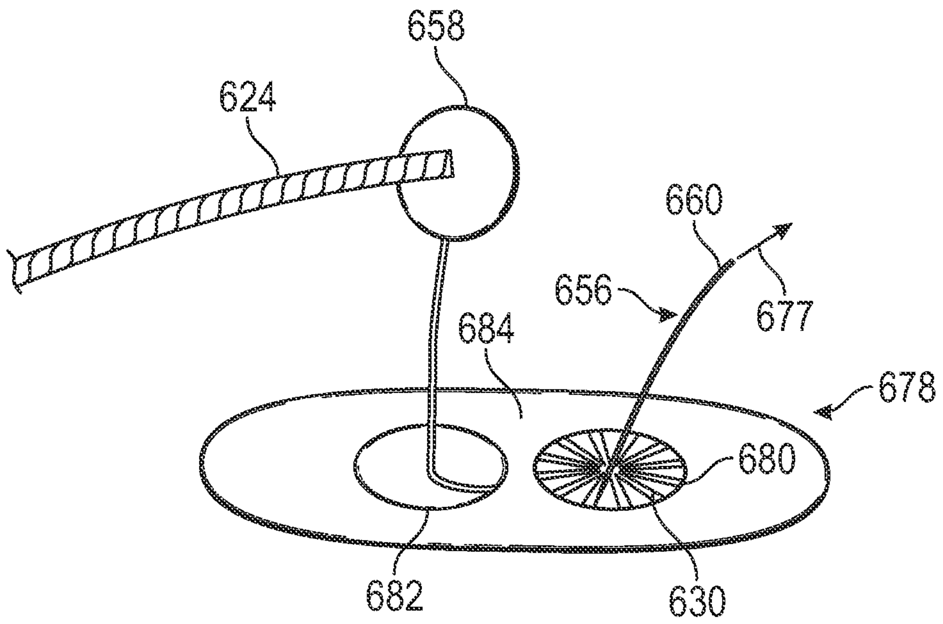
FIG. 25 illustrates an exemplary surgical button.

FIG. 25 illustrates an exemplary surgical button 678, which is another exemplary suture locking device that can be utilized when performing various tensionable knotless surgical procedures (e.g., syndesmosis procedures, etc.). The size, shape, and material-makeup of the surgical button 678 are not intended to limit this disclosure.

The surgical button 678 may include a first opening 680 and a second opening 682 formed through a body of the surgical button 678 and separated by a bridge 684. The first and second openings 680, 682 may establish through-passages for accommodating and locking one or more strands of suture 624 relative to the surgical button 678.

The first opening 680 may include a plurality of locking barbs 630. The locking barbs 630 may establish a one-way locking mechanism for locking the suture 624 relative to the surgical button 678. The second opening 682 may exclude locking barbs and therefore provides a substantially smooth surface that allows the suture 624 to be shuttled through the surgical button 678 prior to being locked in place via the locking barbs 630.

The suture 624 may be shuttled through the second opening 682 and then through the first opening 680 of the surgical button 678 using a shuttle device 656. The shuttle device 656 may be a passing wire or another suture, for example. The suture 624 may be passed through an eyelet 658 of the shuttle device 656, and a free end 660 of the shuttle device 656 may then be pulled (in the direction 677) to shuttle the suture 624 through the surgical button 678.

Figure 26:
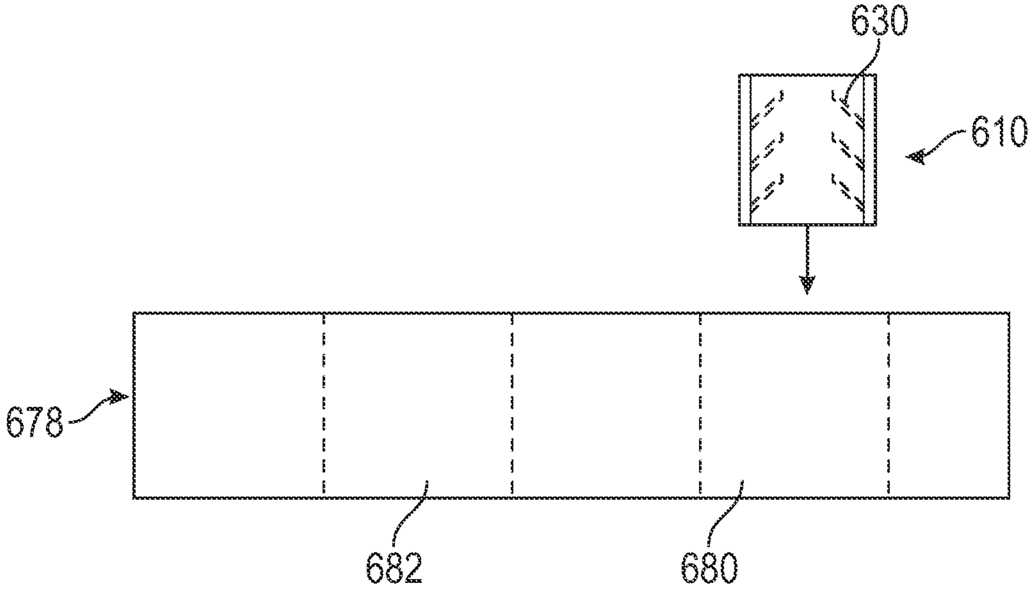
FIG. 26 illustrates another exemplary surgical button.

In the illustrated embodiment, the locking barbs 630 are integrally formed features of the body of the surgical button 678. However, the locking barbs 630 could alternatively be provided within a separate locking ferrule 610 that is insertable into the first opening 680 or the second opening 682 of the surgical button 678 (see, e.g., FIG. 26).

Figure 27:
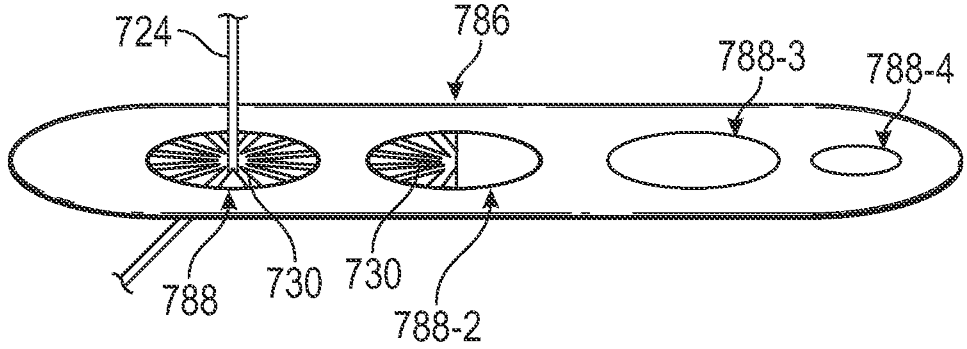
FIG. 27 illustrates an exemplary bone plate.

FIG. 27 illustrates an exemplary bone plate 786, which is another exemplary suture locking device that can be utilized when performing various tensionable knotless surgical procedures (e.g., syndesmosis procedures, clavicle fracture repairs, etc.). The size, shape, and material-makeup of the bone plate 786 are not intended to limit this disclosure.

The bone plate 786 may include a plurality of openings 788 formed through a plate body of the bone plate 786. The openings 788 may establish through-passages for accommodating other devices, such as suture, screws, etc. and/or for locking one or more strands of suture 724 relative to the bone plate 786.

One or more of the openings 788 may include a plurality of locking barbs 730. The locking barbs 730 may establish a one-way locking mechanism for locking the suture 724 relative to the bone plate 786. The suture 724 may be passed through the opening 788 in a first direction and may be prevented from moving in a second direction by the locking barbs 730.

In an embodiment, the locking barbs 730 may only be provided at select portions of the respective opening, with remaining portions left smooth by omitting the locking barbs (see, e.g., opening identified at 788-2). In another embodiment, at least a portion of the openings 788 of the bone plate 786 may completely omit any locking barbs 730 (see, e.g., openings identified at 788-3 and 788-4).

Figure 28:
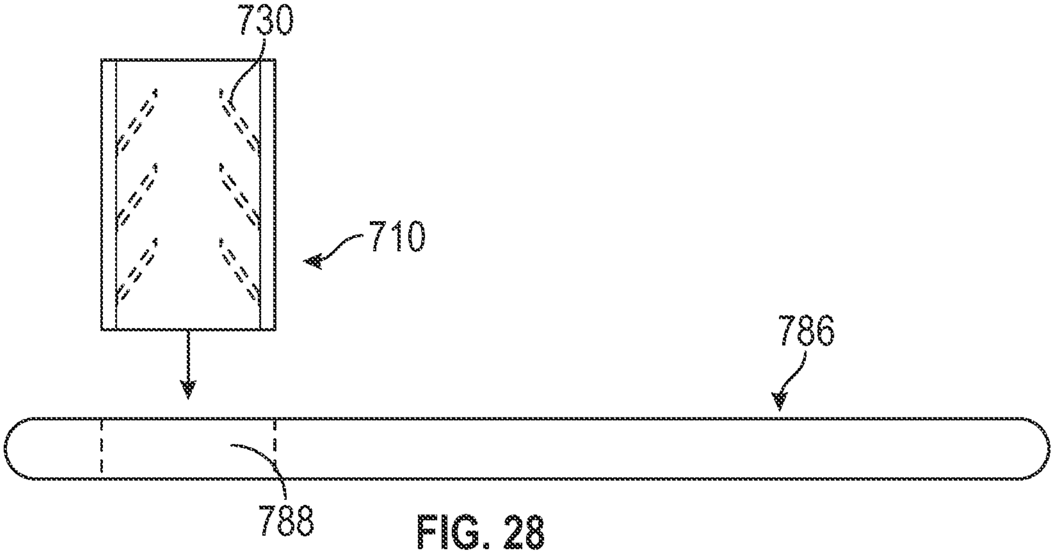
FIG. 28 illustrates another exemplary bone plate.

In the illustrated embodiment, the locking barbs 730 are integrally formed features of the plate body of the bone plate 786. However, the locking barbs 730 could alternatively be provided as part of a separate locking ferrule 710 that is insertable into one of the openings 788 of the bone plate 786 (see, e.g., FIG. 28).

Figure 29:
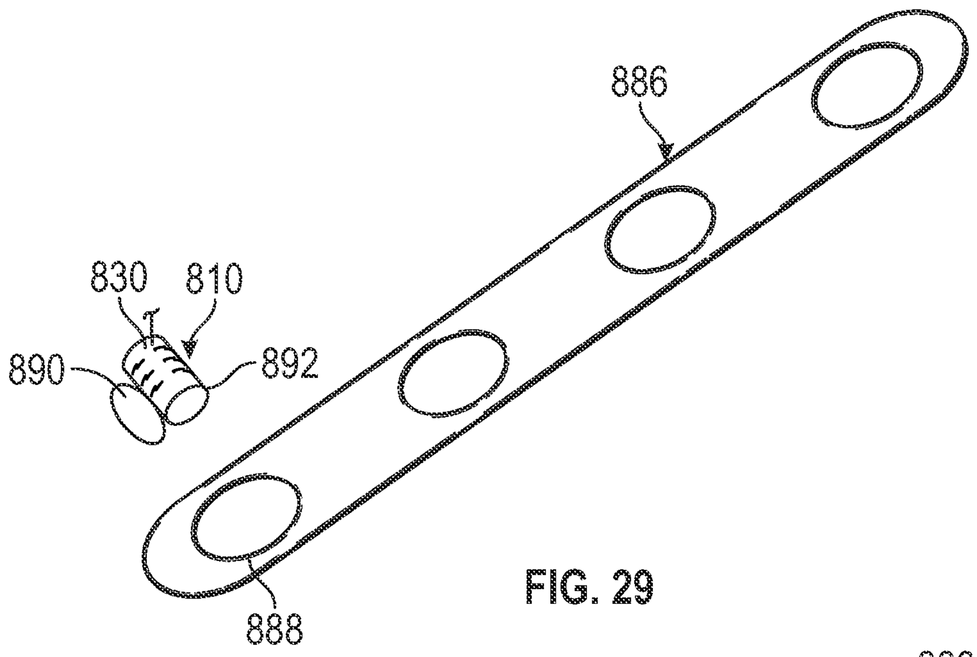
FIG. 29 illustrates another exemplary bone plate.
Figure 30:
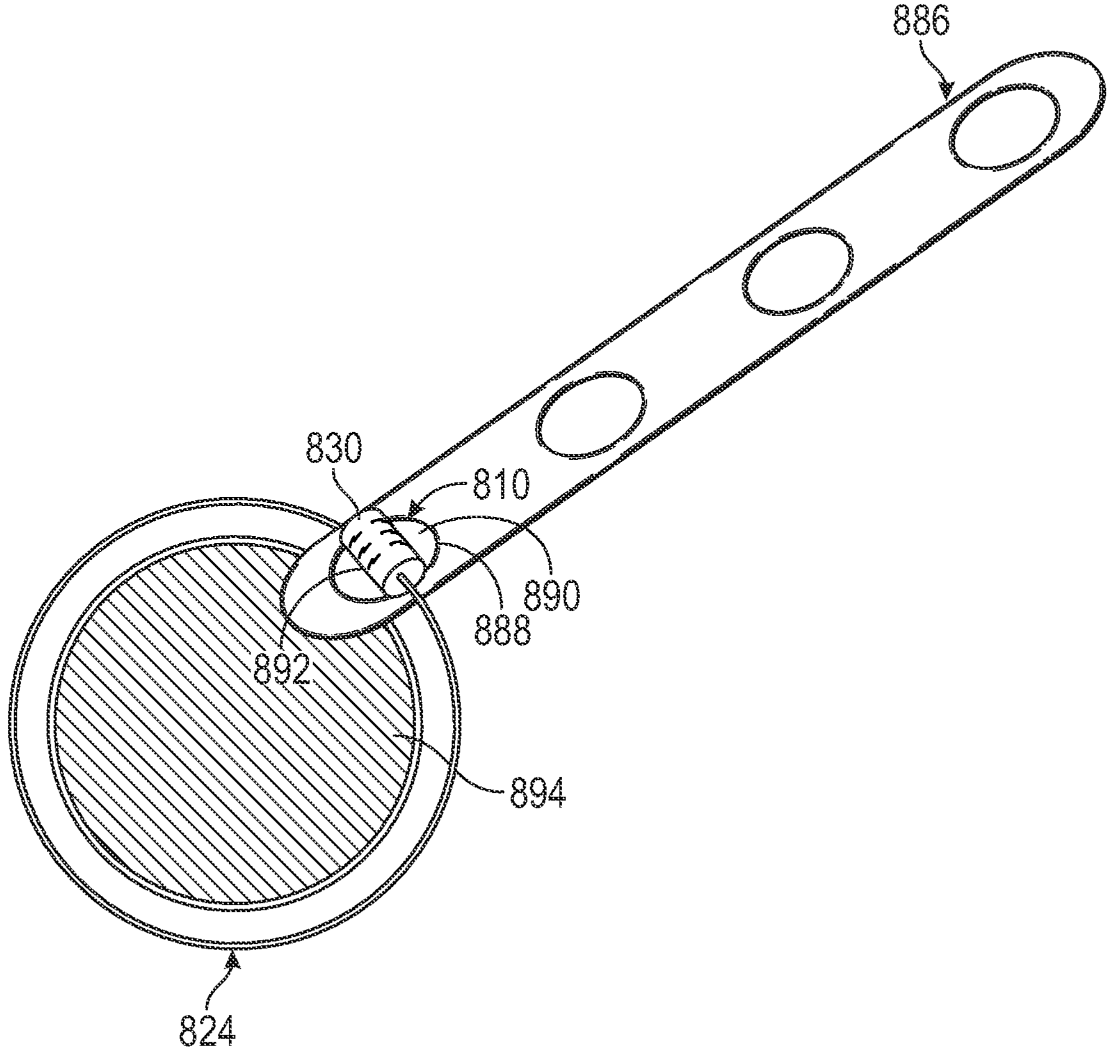
FIG. 30 schematically illustrates locking a suture relative to the bone plate of FIG. 29.

FIGS. 29 and 30 illustrate another exemplary bone plate 886. The bone plate 886 may include one or more openings 888 formed through a plate body of the bone plate 886.

A locking ferrule 810 may be inserted into any one of the openings 888. The locking ferrule 810 may include an engagement portion 890 and an eyelet portion 892. The engagement portion 890 may be configured to connect to the opening 888, such as via a threaded engagement, for example. The eyelet portion 892 may be configured to receive and lock suture 824 relative to the bone plate 886.

The eyelet portion 892 may include a plurality of locking barbs 830. The locking barbs 830 may establish a one-way locking mechanism for locking the suture 824 relative to the bone plate 886. The suture 824 may be passed through the eyelet portion 892 in a first direction and may be prevented from moving in a second direction by the locking barbs 830.

After inserting the locking ferrule 810 into one of the openings 888, the suture 824 may be passed through or around a tissue 894 (e.g., bone, see FIG. 30) and then passed through the eyelet portion 892. The suture 824 may then be tensioned to knotlessly secure the tissue 894 at a desired position relative to the bone plate 886.

Figure 31:
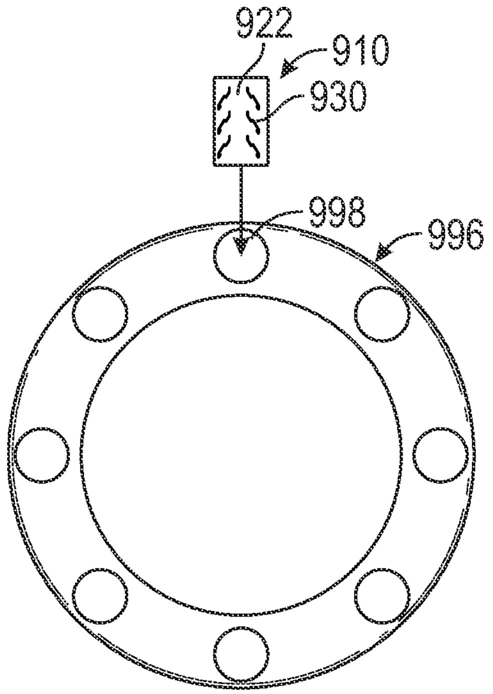
FIG. 31 illustrate an exemplary arthroplasty implant.
Figure 32:
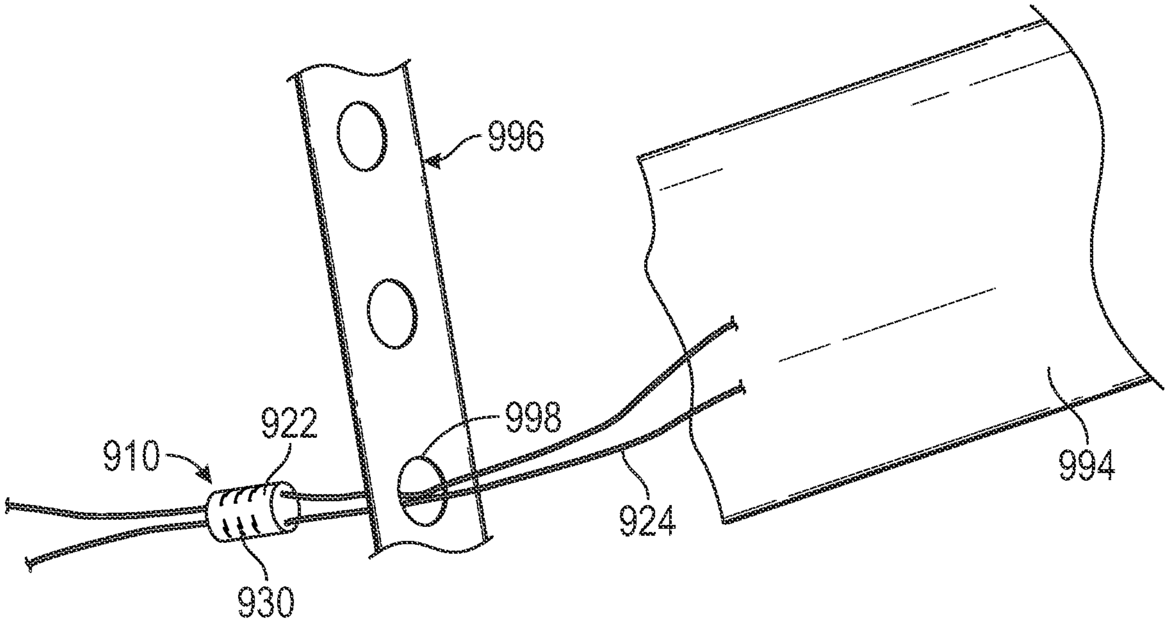
FIG. 32 schematically illustrates locking a suture relative to the arthroplasty implant of FIG. 31.

FIGS. 31 and 32 illustrate an exemplary arthroplasty implant 996, which is another exemplary suture locking device that can be utilized when performing various tensionable knotless surgical procedures (e.g., shoulder arthroplasty procedures, etc.). The size, shape, and material-makeup of the arthroplasty implant 996 are not intended to limit this disclosure.

The arthroplasty implant 996 may include one or more openings 988 formed through a body of the arthroplasty implant 996. A locking ferrule 910 may be inserted into any one of the openings 988. The locking ferrule 910 may include a cannulation 922 that includes a plurality of locking barbs 930. The locking barbs 930 may establish a one-way locking mechanism for locking the suture 924 relative to the locking ferrule 910.

In an embodiment, the suture 924 may be passed through or around a tissue 994 (e.g., tendon, see FIG. 32), be passed through the opening 988, and then be passed through the cannulation 922 of the locking ferrule 910. The suture 924 may then be tensioned to knotlessly secure the tissue 994 at a desired position relative to the arthroplasty implant 996.

Figure 33:
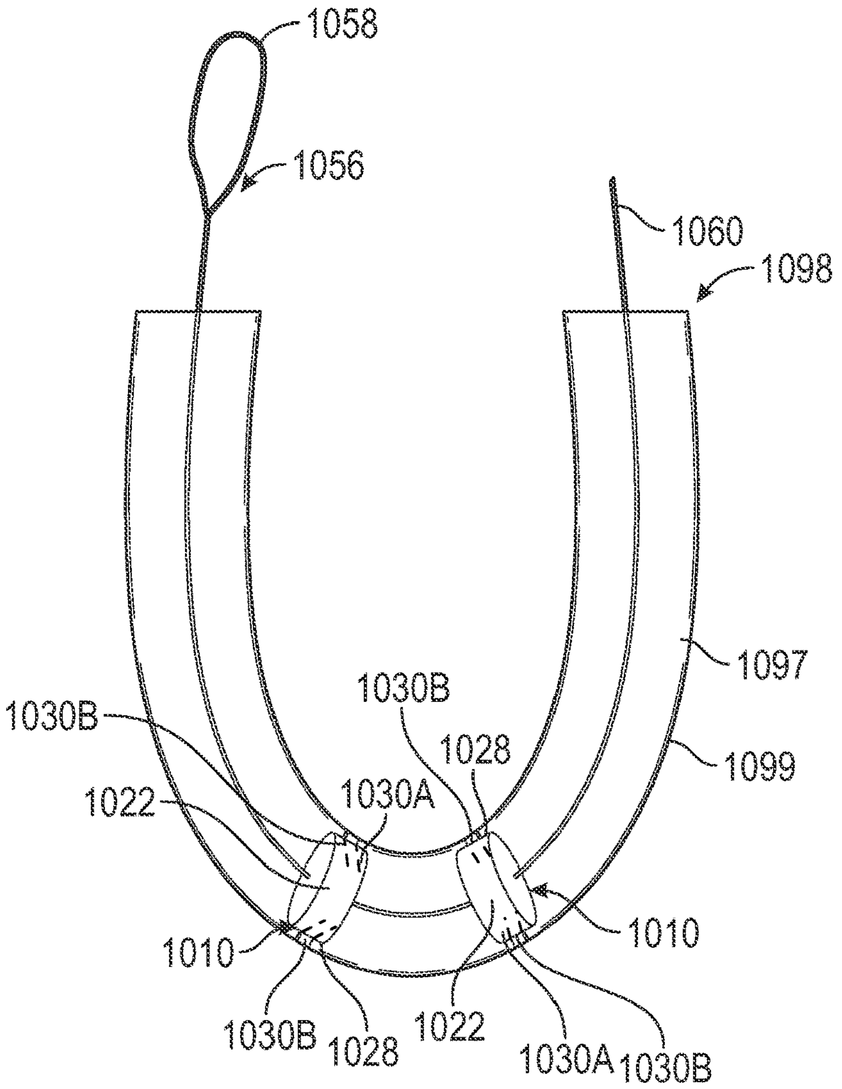
FIG. 33 illustrates an exemplary suture anchor.
Figure 34:
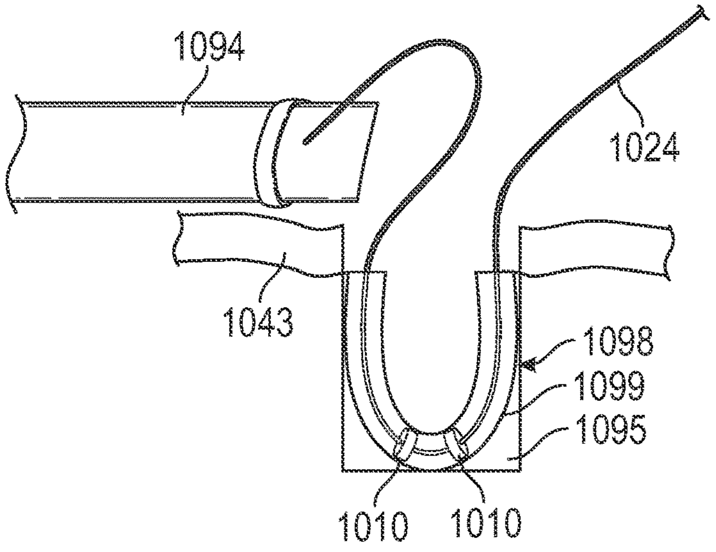
FIG. 34 schematically illustrates a surgical method for performing a tissue repair.

FIGS. 33 and 34 illustrate an exemplary suture anchor 1098, which is another exemplary suture locking device that can be utilized when performing various tensionable knotless surgical procedures (e.g., soft tissue-to-bone fixation, etc.). The suture anchor 1098 may include a sheath 1099 and a shuttle device 1056 received through the sheath 1099. The sheath 1099 may be a “soft” body made exclusively of soft, suture-based materials. The shuttle device 1056 may be a passing wire or another suture, for example.

The suture anchor 1098 may additionally include one or more locking ferrules 1010 that may be positioned within an internal bore 1097 of the sheath 1099. Each locking ferrule 1010 may include a cannulation 1022 that includes a first plurality of locking barbs 1030A. The locking barbs 1030A may establish a one-way locking mechanism for locking suture 1024 relative to the locking ferrule 1010. An outer diameter wall 1028 of the locking ferrule 1010 may include a second plurality of barbs 1030B that are configured to engage the internal wall of the sheath 1099 for locking a position of the locking ferrule 1010 within the internal bore 1097.

In an embodiment, the sheath 1099 of the suture anchor 1098 may be inserted into a socket 1095 formed in a bone 1093. The socket 1095 may be a preformed opening formed in the bone 1093 that is sized for receiving the sheath 1099. The suture 1024 may be passed through or around a tissue 1094 (e.g., ligament, tendon, etc., see FIG. 34) and may then be passed through an eyelet 1058 of the shuttle device 1056. A free end 1060 of the shuttle device 1056 may then be pulled to shuttle the suture 1024 through the sheath 1099. The suture 1024 may then be further tensioned to knotlessly secure the tissue 1094 at a desired position relative to the bone 1093.

Figure 35:
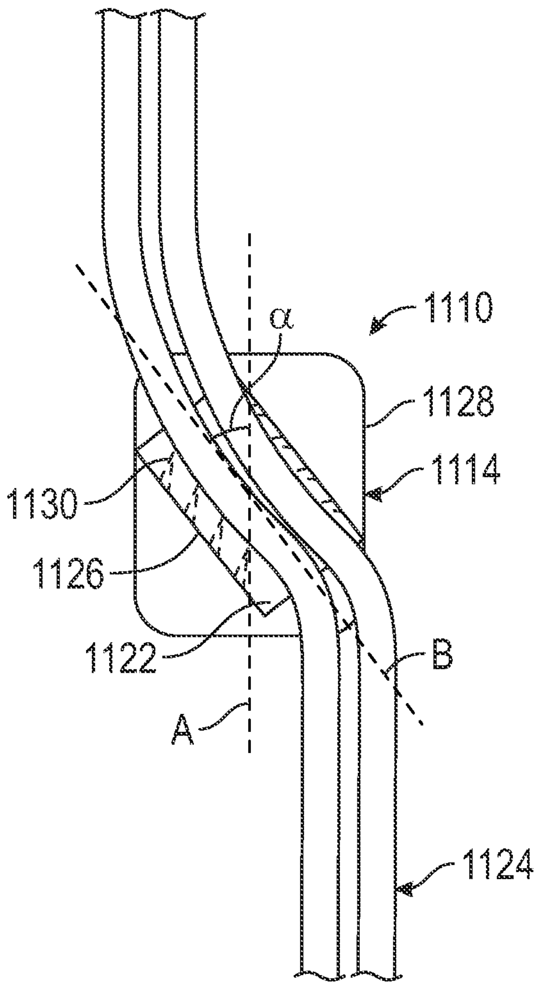
FIG. 35 illustrates yet another exemplary locking ferrule.

FIG. 35 illustrates another exemplary locking ferrule 1110 that includes a barrel portion 1114, which may be provided either with or without an integrated cap portion. A cannulation 1122 may extend through the barrel portion 1114 and may establish an internal passageway for accommodating one or more strands of suture 1124. The cannulation 1122 may be circumscribed by an interior wall 1126 of the locking ferrule 1110. An outer diameter wall 1128 of the barrel portion 1114 may be smooth or could alternatively include threads, barbs, or other features for facilitating bone fixation.

A plurality of locking barbs 1130 may protrude inwardly from the interior wall 1126. The locking barbs 1130 may therefore occupy at least a portion of the open space of the cannulation 1122. The locking barbs 1130 may establish a one-way locking mechanism that permits suture 1124 to pass through the cannulation 1122 in a first direction while preventing the suture 1124 from being tensioned or otherwise moved in a second direction.

In an embodiment, the cannulation 1122 may extend along a longitudinal centerline axis B that extends at an oblique angle $\alpha$ relative to a longitudinal centerline axis A of the barrel portion 1114. Arranging the cannulation 1122 at the oblique angle $\alpha$ through the locking ferrule 1110 can help force the suture 1124 into increased engagement with the locking barbs 1130.

The suture locking devices of this disclosure may be utilized for performing various tensionable knotless surgical repairs or other surgical procedures. The suture locking devices provide for tensioning and retensioning suture(s) at various points of the repair, including subsequent to implantation of accompanying fixation devices, thus providing numerous advantages over prior tissue repair systems and techniques.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A suture locking device, comprising:

a suture anchor having a soft, suture-based sheath that includes an internal bore; and a locking ferrule positioned within the internal bore of the soft, suture-based sheath and including a one-way locking mechanism configured for locking a suture relative to the suture anchor.

2. The suture locking device as recited in claim 1, wherein the one-way locking mechanism is configured to allow the suture to be tensioned in a first direction and prevent the suture from moving in a second direction.

3. The suture locking device as recited in claim 2, wherein the one-way locking mechanism is established by a plurality of locking barbs provided within a cannulation of the locking ferrule.

4. The suture locking device as recited in claim 3, wherein the cannulation extends through a tubular body of the locking ferrule.

5. The suture locking device as recited in claim 4, wherein the plurality of locking barbs are each angled in a common direction within the cannulation.

6. The suture locking device as recited in claim 3, wherein the plurality of locking barbs are arranged in at least a first row and a second row along the cannulation.

7. The suture locking device as recited in claim 6, wherein a first portion of the plurality of locking barbs of the first row are staggered relative to a second portion of the plurality of locking barbs of the second row.

8. The suture locking device as recited in claim 3, wherein the locking ferrule includes a second plurality of barbs provided at an outer diameter wall of the locking ferrule.

9. The suture locking device as recited in claim 1, wherein the internal bore extends through the soft, suture-based sheath of the suture anchor.

10. The suture locking device as recited in claim 9, wherein an outer diameter wall of the locking ferrule includes a second plurality of barbs that are configured to engage an internal wall of the soft, suture-based sheath.

11. The suture locking device as recited in claim 9, comprising a shuttle device received through the soft, suture-based sheath and configured to shuttle the suture through the soft, suture-based sheath and the locking ferrule.

12. The suture locking device as recited in claim 11, wherein the shuttle device is a shuttle suture.

13. The suture locking device as recited in claim 12, wherein the suture is connected to an eyelet of the shuttle suture.

14. The suture locking device as recited in claim 1, wherein the suture includes a varying thickness.

15. The suture locking device as recited in claim 14, wherein the suture includes at least one tapered region where the suture transitions between a thickened section and a thinned section.

16. The suture locking device as recited in claim 1, wherein the locking ferrule includes a unitary tubular body, a cannulation extends through the unitary tubular body, and the one-way locking mechanism includes a plurality of locking barbs that are each angled in a common direction along an interior wall of the cannulation.

17. A suture locking device as, comprising:

a suture anchor including an internal bore;

a locking ferrule positioned within the internal bore and including a one-way locking mechanism configured for locking a suture relative to the suture anchor, wherein the internal bore extends through a sheath of the suture anchor, and wherein the sheath is a soft body made exclusively of soft, suture-based materials.

18. A suture locking device, comprising:

a soft suture anchor sheath comprised exclusively of suture-based materials; and a locking ferrule positioned within an internal bore that extends through the soft suture anchor sheath, the locking ferrule including a plurality of angled locking barbs configured to permit a suture to be tensioned in a first direction while preventing movement of the suture in a second, opposite direction relative to the soft suture anchor sheath.

19. The suture locking device as recited in claim 18, comprising a shuttle suture received through the internal bore and being tensionable to shuttle the suture through the locking ferrule.

20. The suture locking device as recited in claim 18, wherein the locking ferrule includes a unitary tubular body, a cannulation extends through the unitary tubular body, and the plurality of angled locking barbs are each angled in a common direction along an interior wall of the cannulation.

* * * * *